US012583834B2

(12) United States Patent
Rama Rao et al.

(10) Patent No.: US 12,583,834 B2
(45) Date of Patent: Mar. 24, 2026

(54) METHOD OF TREATING BACTERIAL INFECTIONS AND PHARMACEUTICAL COMPOSITION FOR TREATING BACTERIAL INFECTIONS

(71) Applicant: Institut National de Recherche pour l'Agriculture, l'Alimentation et l'Environnement, Paris (FR)

(72) Inventors: Nalini Rama Rao, Buc (FR); Seav-Ly Tran, Paris (FR)

(73) Assignee: INSTITUT NATIONAL DE RECHERCHE POUR L'AGRICULTURE, L'ALIMENTATION ET L'ENVIRONNEMENT, Paris (FR)

( * ) Notice: Subject to any disclaimer, the term of this patent is extended or adjusted under 35 U.S.C. 154(b) by 771 days.

(21) Appl. No.: 17/904,696

(22) PCT Filed: Feb. 19, 2021

(86) PCT No.: PCT/EP2021/054136
§ 371 (c)(1),
(2) Date: Aug. 19, 2022

(87) PCT Pub. No.: WO2021/165463
PCT Pub. Date: Aug. 26, 2021

(65) Prior Publication Data

US 2023/0116468 A1 Apr. 13, 2023

(30) Foreign Application Priority Data

Feb. 21, 2020 (EP) .................................... 20305172

(51) Int. Cl.

| | |
|---|---|
| ***C07D 401/04*** | (2006.01) |
| ***A61K 9/51*** | (2006.01) |
| ***A61P 31/04*** | (2006.01) |

(52) U.S. Cl.
CPC ............ *C07D 401/04* (2013.01); *A61P 31/04* (2018.01); *A61K 9/51* (2013.01)

(58) Field of Classification Search
CPC .... C07D 401/04; A61K 9/51; A61K 31/4184; A61K 31/435; A61P 31/04
See application file for complete search history.

(56) References Cited

FOREIGN PATENT DOCUMENTS

| | | | | |
|---|---|---|---|---|
| WO | 03037890 A2 | 5/2003 | | |
| WO | 2005113542 A2 | 12/2005 | | |
| WO | 2017191184 A1 | 11/2017 | | |
| WO | 2018042377 A1 | 3/2018 | | |
| WO | WO-2019166639 A1 * | 9/2019 | ......... | A61K 31/4709 |

OTHER PUBLICATIONS

Hellwinkel, D.; Systematic Nomenclature of Organic Chemistry, Section 2.2.2, pp. 84-85; Springer-Verlag, Heidelberg, 2001 (Year: 2001).*
Cheow, et al.; Colloids and Surfaces B: Biointerfaces, v85, pp. 214-220; 2011 (Year: 2011).*
Chemical Abstracts Service, "2094576-12-0", Registry May 2, 2017, Database accession No. 2094576-12-0 Retrieved from the Internet: URL:Chemical Abstracts Service, Columbus, Ohio, US.
Bijivemula N. Reddy et al., "Novel 7-Nitro-1-(Piperidin-4-yl)-4,5-Dihydro-[1,2,4] Triazolo[4,3-a]Quinoline-Sulphonamide Derivatives as Antimicrobial Agents: Design, Synthesis, and Bio-Activity : 7-Nitro-1-(Piperidin-4-yl)-4,5-Dihydro-[1,2,4] Triazolo[4,3-a]Quinoline-Sulphonamide Derivatives", Journal of Heterocyclic Chemistry, vol. 53, No. 5, Sep. 1, 2016, p. 1416-1423.
Claire Darrigo et al, "The Bacterial Mfd Protein Prevents DNA Damage Induced by the Host Nitrogen Immune Response in a NER-Independent but RecBC-Dependent Pathway", PLOS ONE, vol. 11, No. 10, Oct. 6, 2016, p. e0163321.
International Search Report and Written Opinion mailed, May 18, 2021, for PCT/EP2021/054136.

* cited by examiner

*Primary Examiner* — Jeffrey S Lundgren
*Assistant Examiner* — W. Justin Youngblood
(74) *Attorney, Agent, or Firm* — ArentFox Schiff LLP

(57) ABSTRACT

The invention relates to a compound having the general formula (I), or one of the pharmaceutically acceptable salts thereof, for it use as a medicament, in particular for treating a bacterial infection in a subject:

(I)

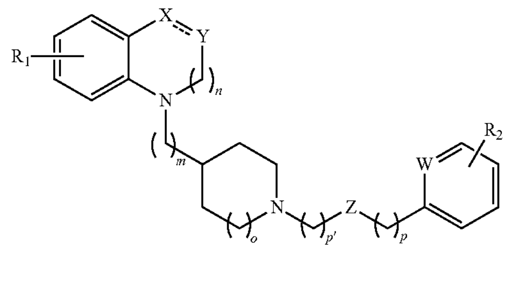

In particular, this compound is capable of inhibiting the Mfd activity of bacteria.

14 Claims, 3 Drawing Sheets

FIG 7
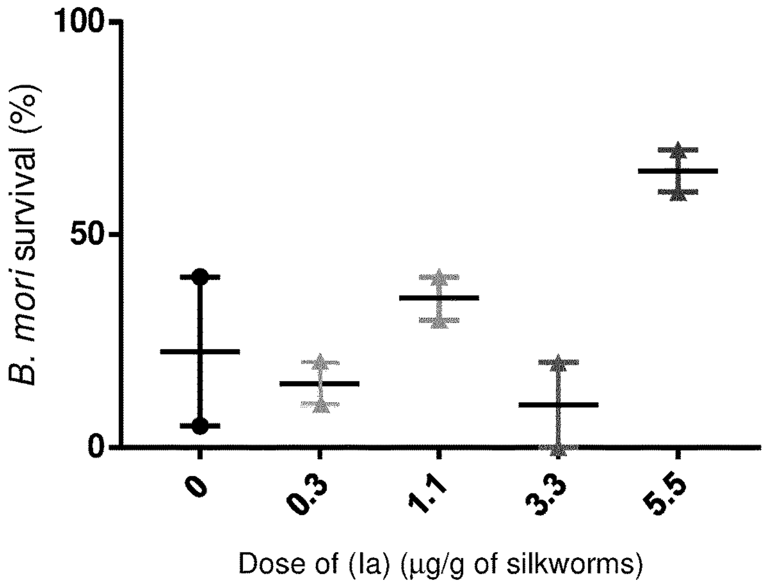
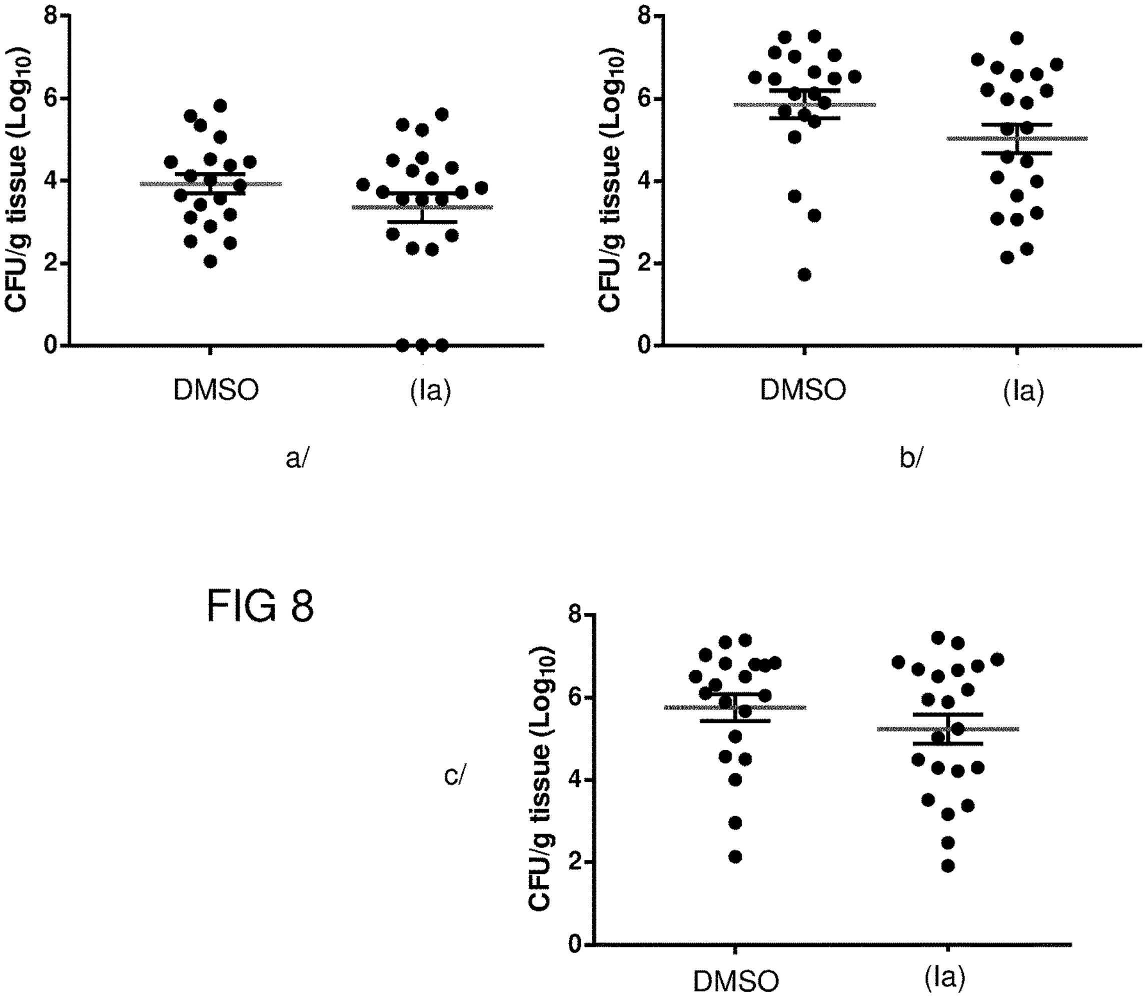
FIG 8

METHOD OF TREATING BACTERIAL INFECTIONS AND PHARMACEUTICAL COMPOSITION FOR TREATING BACTERIAL INFECTIONS

CROSS-REFERENCE TO RELATED APPLICATIONS

This application is a National Phase of PCT/EP2021/054136, filed on Feb. 19, 2021, which claims priority to EP Application Serial No. 20305172.7, filed on Feb. 21, 2020, the disclosures of which are hereby incorporated by reference in their entireties.

The invention lies in the field of therapeutics, in particular of the treatment of bacterial infections.

More particularly, the invention relates to the use of a compound having a particular chemical formula as a medicament, in particular for treating bacterial infections. The invention also relates to a pharmaceutical composition containing such a compound, as well as to the use of this pharmaceutical composition for treating bacterial infections.

In the last decades, antibiotics have drastically reduced the mortality associated with infectious diseases in humans and animals. Yet, their effectiveness and easy access led to misuse and overuse, prompting bacteria to develop resistance, resulting in a dramatic health issue. For example, in Europe, antibiotics-resistant bacterial infections cause tens of thousands of deaths each year.

New medicines are thus urgently needed for efficiently treating bacterial infections.

Some research works have been conducted in the last years in order to identify and characterize new bacterial targets and to develop new drugs specific to these targets for efficiently fighting against bacterial infections while being associated with a reduced risk of apparition of bacterial resistance.

Some of these works were based on the fact that the host's defense against bacteria is primarily provided by the host's immune system. Nitric oxide in particular, which is produced in excess by the host's phagocytic and epithelial cells during a bacterial infection, plays an important role for fighting the infection, by limiting bacterial proliferation and contributing to bacterial clearance.

In this context, a new bacterial target, the Mfd (for Mutation Frequency Decline) protein, has been identified by the prior art. Mfd is a Transcription Repair Coupling Factor, widely conserved amongst bacteria and absent in eukaryotes.

Mfd recognizes RNA polymerase stalled at non-coding lesions, uses the energy from ATP hydrolysis to disrupt the transcription complex, and stimulates DNA repair by recruiting components of the nucleotide excision repair machinery (Deaconescu et al., 2006, Cell 124: 507-520).

It was shown by the prior art, illustrated by the publication of Guillemet et al., 2016, Sci Rep 6: 29349 and the publication of Darrigo et al., 2016, PLoS ONE 11, e0163321, that Mfd is involved in bacterial pathogenesis, and more specifically that: mfd deficient mutants of two divergent intestinal bacteria, *Bacillus cereus* and *Shigella flexneri*, are affected in their virulence and ability to survive in a mouse model of infection; Mfd confers bacterial resistance to nitric oxide, a major toxic component of the host innate immune system; nitric oxide induces bacterial DNA damage and Mfd repairs these lesions. As Mfd is widely conserved, it might be used by a large spectrum of bacteria to overcome the host immune response.

Mfd has therefore been identified as a promising target for the development of new and innovative antimicrobial strategies, as molecules inhibiting Mfd activity would prevent resistance of the bacteria to the host immune response, thus leading to pathogenic bacterial elimination by the host.

WO 2017/191184 discloses a method of in vitro and in silico screening of antibacterial molecules for their capacity of inhibiting Mfd activity in pathogenic bacteria.

The present invention aims at providing a compound capable of inhibiting the Mfd activity of bacteria, in particular of a bacterial pathogen infecting a living subject, in order to efficiently treat bacterial infections.

Other objectives of the invention are that this compound is not toxic to the subject, and that there is the least possible risk that bacteria develop resistance against it.

It has now been discovered by the inventors that these objectives are achieved by compounds having a specific chemical formula.

Therefore, according to a first aspect, the invention relates to a compound having the general formula (I):

(I)

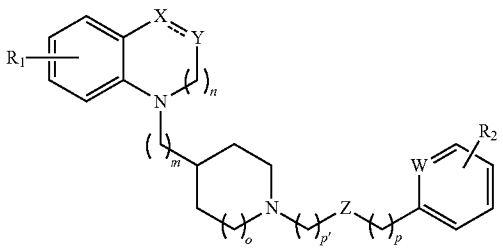

wherein m is an integer between 0 and 2, n is equal to 0 or 1, is equal to 0 or 1, p is an integer between 0 and 2, p' is an integer between 0 and 2, either the double line ------ represents a single bond and X is selected in the group consisting of an oxygen atom, $CH_2$, NH, N—$R_5$ and —NCO—$R_5$, wherein $R_5$ represents a linear, branched and/or cyclic, saturated or unsaturated, hydrocarbon-based radical, optionally substituted, optionally comprising one or several heteroatoms and/or one or more groups containing one or more heteroatoms, and Y represents a methylene group or a carbonyl group, a thiocarbonyl group (C═S) or a C≡N—$R_9$ group wherein $R_9$ represents a hydrogen atom or an alkyl or aryl group, or the double line ------ represents a double bond and X represents a nitrogen atom and Y represents a methine group, X and Y then representing together a moiety of formula:

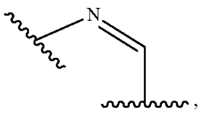 [SMILES: */C=N\*]

Z represents a covalent bond, a methylene group, a sulfonyl group, an amide group, an ester group, an ether group or a carbonyl group, provided that Z does not represent a carbonyl group when p is equal to 0, W represents a nitrogen atom or a C—$R_{10}$ group wherein $R_{10}$ represents a hydrogen atom or a linear, branched and/or cyclic, saturated or unsaturated, hydrocarbon-based radical, optionally substituted, optionally comprising one or several heteroatoms and/or one or more groups containing one or more heteroatoms, $R_1$ is selected in the group consisting of a hydrogen atom, a halogen atom, a hydroxyl group, a primary amine group, a linear or branched and/or cyclic saturated or unsaturated carbon-based radical, optionally aromatic, optionally substituted, optionally comprising one or several heteroatoms and/or one or more groups containing one or more heteroatoms, a —O—$R_6$, —NH—$R_6$ or —NH—CO—$R_6$ group wherein $R_6$ represents a linear, branched and/or cyclic, saturated or unsaturated, hydrocarbon-based radical, optionally substituted, optionally comprising one or several heteroatoms and/or one or more groups containing one or more heteroatoms, or a —$NR_7RB$ group wherein $R_7$ and $R_8$, which may be identical or different, each represent a linear, branched and/or cyclic, saturated or unsaturated, hydrocarbon-based radical, optionally substituted, optionally comprising one or several heteroatoms and/or one or more groups containing one or more heteroatoms, and $R_2$ is selected in the group consisting of a hydrogen atom, a halogen atom, a hydroxyl group, a sulfonic acid group, a primary amine group, and a linear, branched and/or cyclic, saturated or unsaturated, carbon-based radical, optionally substituted, optionally aromatic, optionally comprising one or several heteroatoms and/or one or more groups containing one or more heteroatoms, or one of the pharmaceutically acceptable salts thereof, for its use as a medicament, in particular for treating a bacterial infection in a subject.

The treated subject, which is suffering of a bacterial infection or likely to get infected, is preferably a mammalian subject. It may be an animal or a human subject.

By "pharmaceutically acceptable salt" it is meant in the present description any salt of the compound having, as a counterion, a species that produces no adverse, allergic or other undesirable reaction when it is administered to a subject, in particular to a mammal.

According to the invention, the compound of formula (I) may be used as such or as a solvate.

The term "treating" is used herein to refer to obtaining a desired pharmacological and physiological effect. This effect may be prophylactic or curative. The term "treating" as used herein therefore includes preventing or partially preventing a disease, symptom or condition thereof from occurring in a subject which has not yet been diagnosed as having the disease; and/or partially or completely curing a disease, symptom or condition thereof, or an adverse effect attributed to the disease.

In a particular embodiment of the invention, the compound of formula (I) or a pharmaceutically acceptable salt thereof is used for inhibiting the Mfd activity of a pathogenic bacteria infecting the subject.

It has indeed been discovered by the inventors that the compounds having the specific general formula (I), and their pharmaceutically acceptable salts, strongly inhibit the ATPase activity of the Mfd protein of bacteria belonging to very broad range of species, in a dose-dependent way. This inhibition effect leads to an inactivation of the protein and to a sharp decrease of the resistance of the bacteria to nitric oxide. The compound of the invention therefore advantageously enhances the innate immune response of the host with respect to bacterial infections.

As nitric oxide reaches its target molecule by diffusion without requiring any specific receptor, the compound of the invention even allows for an efficient treatment of immunocompromised patients, who usually at least partially react to infection through innate immunity.

The apparition of resistance towards the compound of the invention is advantageously low, as the bacterial selective pressure is narrowed within the inflammation zone.

Furthermore, the compound of the invention is not toxic to the treated subject, in particular as eukaryotes do not possess a Mfd protein.

In particular embodiments of the invention, in formula (I) X is selected in the group consisting of $CH_2$, NH, N-alkyl and NCO-alkyl, said alkyl group being optionally substituted.

In particular embodiments, in formula (I), $R_1$ is selected in the group consisting of a hydrogen atom, a halogen atom, a hydroxyl group, a carbonitrile group, a trifluoromethyl group, a carboxyl group, a primary amine group and an alkyl, alkoxy, aryl, arylalkyl, acyl, —CO—O-alkyl, —NH-alkyl or —NH—CO-alkyl group, all of which may optionally be substituted.

In particular embodiments, the compound of the invention has at least one, preferably a plurality, of the features below:

m is equal to 0;

n is equal to 0;

o is equal to 1;

p is equal to 0;

p' is equal to 0;

X represents a secondary amine group NH;

Y represents a methylene group —$CH_2$,

Z represents a sulfonyl group —$SO_2$—;

W represents CH;

and/or $R_1$ represents a hydrogen atom.

In particular embodiments, $R_2$ is selected in the group consisting of hydrogen, halogen, hydroxyl, alkyl, carbonitrile, trifluoromethyl, alkoxy, aryl, arylalkyl, acyl, carbonyl, carboxyl, sulfonic acid, amine, in particular primary amine, —CO—O-alkyl, —NH-alkyl, —NH—CO-alkyl and —$SO_2$—$NR_3R_4$ wherein $R_3$ and Ra are identical or different linear or branched alkyl groups or $R_3$ and Ra are linked to form a ring together with the nitrogen atom to which they are attached; all of which may optionally be substituted.

In preferred embodiments of the invention $R_2$ represents a —$SO_2$—$NR_3R_4$ group, wherein $R_3$ and $R_4$ are identical or different linear or branched alkyl groups, preferably C1-C6 alkyl groups.

$R_2$ preferably represents —$SO_2$—$N(Me)_2$, wherein $R_3$ and $R_4$ each represent a methyl group.

In other embodiments of the invention $R_3$ and $R_4$ are linked to form, together with the nitrogen atom to which they are attached, a hydrocarbon-based, optionally substituted, five- or six-membered ring, which may optionally comprise one or more additional heteroatoms.

Any combination of one or several of the above features falls within the scope of the invention.

A particular compound that may be used according to the invention is N,N-dimethyl-4-{[4-(2-oxo-2,3-dihydro-1H-1,3-benzodiazol-1-yl)piperidin-1-yl]sulfonyl}benzene-1-sulfonamide, having formula (Ia), or one of the pharmaceutically acceptable salts thereof:

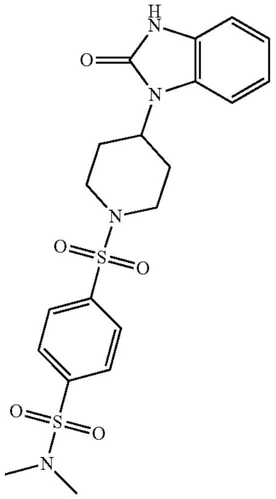

(Ia)

As demonstrated in the examples presented herein below, the compound of formula (Ia), in particular:

- has a strong antibacterial effect against bacteria in conditions of nitric oxide stress, both for Gram-positive bacteria such as of the species *Bacillus cereus* and for Gram-negative bacteria such as of the species *Klebsiella pneumoniae* and *Acinetobacter baumanii*. This is all the more advantageous that these two last species have been listed as priority for research and development of antibacterial therapeutic by the World Health Organization;
- increases insect survival upon infection with both Gram-positive bacteria such as of the species *Bacillus cereus* and Gram-negative bacteria such as of the species *Pseudomonas aeruginosa;*
- decreases the bacterial load in various organs following infection of a mouse model by *Bacillus cereus.*

The bacterial infection treated by the compound of the invention may be caused by Gram-negative and/or Gram-positive bacteria, in particular by pathogenic bacteria, such as human pathogenic bacteria.

The invention is particularly useful for treating infections by bacteria that are resistant to conventional antibiotics.

The bacteria causing the infection may for example belong to the following genera: *Bacillus*, such as *Bacillus cereus, Shigella, Salmonella, Clostridium, Staphylococcus, Klebsiella*, such as *Klebsiella pneumoniae, Escherichia*, such as *Escherichia coli, Neisseria, Yersinia, Listeria, Streptococcus, Mycobacterium, Chlamydia, Helicobacter, Acinetobacter*, such as *Acinetobacter baumanii, Pseudomonas*, such as *Pseudomonas aeruginosa*, etc.

The compound of the invention is preferably administrated to the subject in a therapeutically-effective amount.

By "therapeutically-effective amount" it is herein meant the amount of a compound that, when administered to a subject for treating a disease, is sufficient to perform such treatment of the disease.

The therapeutically-effective amount of the compound will depend on several factors, such as the disease and its severity, in particular the bacterial species causing the infection, the age, weight, etc., of the subject to be treated, the particular compound used, the route and form of administration, etc. The therapeutically-effective amount of the compound of the invention will be determined by the practitioner for each individual case.

The compound of the invention may be administered to the subject by any administration route that is classical per se. The compound of the invention may for example be administered to the subject in need thereof by oral, parenteral, topical, intranasal, rectal or pulmonary (e.g. by aerosol, inhalation, etc.) route.

Parenteral administration routes include subcutaneous, subdural, intravenous, intramuscular, intrathecal, intraperitoneal, intracerebral, intraarterial and intralesional routes of administration.

The compound of the invention is preferentially administrated to the subject by oral or intravenous route.

As for the posology of administration, its exact determination falls within the skills of the skilled practitioner. The compound of the invention may for example be administrated to the subject in need thereof once or twice daily, for example during a period of a few days to a few weeks.

The invention may also be expressed in the terms of a method of therapeutically treating a subject suffering from a disease, in particular from a bacterial infection, said method comprising administering to said subject in need thereof a therapeutically-effective amount of a compound of the invention. This method may have any of the features or combination of features described above.

The invention also relates to the use of a compound according to the invention for the manufacture of a medicament, in particular a medicament for treating a bacterial infection. This use may respond to any of the features or combination of features described herein above.

Another object of the invention is a pharmaceutical composition comprising a compound according to the invention, as defined above, i.e. a compound of formula (I) or one of its pharmaceutically acceptable salts, as an active agent, in a pharmaceutically acceptable vehicle.

A "pharmaceutically acceptable vehicle" herein means a vehicle that is useful in preparing a pharmaceutical composition or formulation and that is generally safe, non-toxic, and neither biologically nor otherwise undesirable for the subject to be treated, in particular humans and/or animals.

The vehicle of the composition of the invention may be solid, semi-solid or liquid. It may be a diluent, an adjuvant or any other vehicle conventional per se for the constitution of pharmaceutical compositions.

The pharmaceutical composition of the invention may comprise one or more excipients/additives conventional by themselves, for example preservatives, sweetening agents, flavoring agents, filling agents, disintegrating agents, wetting agents, emulsifying agents, suspending agents, dispersing agents, lubricating agents, stabilizing agents, buffering agents, tonicity modifiers, antifungal agents, antibodies such as IgG, etc., or any of their mixtures; and/or any agent providing quick, sustained, or delayed-release of the compound of the invention after administration to the patient.

The pharmaceutical composition of the invention may be formulated in any galenical form, in particular in a form that is suitable for administration in mammals, and in particular in humans, and more particularly in a form that is suitable for administration by oral, parenteral, topical, intranasal, rectal or pulmonary route.

The pharmaceutical composition of the invention is preferably formulated in a form that is suitable for administration by oral or intravenous route.

The pharmaceutical composition of the invention may for example be in a form that is suitable for oral administration, such as in the form of granulates, powder, syrup, tablets, capsules, pills, oral solution or suspension; or else in the form of suppositories, injectable solution, aerosol, ointment, etc.

The pharmaceutical composition of the invention may also contain one or more other active agents, which may or may not act in synergy with the compound of the invention, for example an anti-inflammatory agent and/or a pain-relieving agent, or else an antimicrobial agent.

In particular embodiments of the invention the compound of the invention is encapsulated in an encapsulating agent improving its bioavailability, in particular in nanoparticles.

The pharmaceutical composition of the invention is preferably formulated in a unit dosage form, each dosage containing from about 1 to 10 mg of the compound of the invention.

The invention also relates to the therapeutic use of a pharmaceutical composition as herein defined, in particular for treating a bacterial infection in a subject, in particular a mammal and more particularly a human or an animal.

The pharmaceutical composition of the invention may be used for inhibiting the Mfd activity of a pathogenic bacteria infecting the subject to be treated.

This use of the pharmaceutical composition of the invention may respond to any of the features described herein above in relation with the therapeutic use of the compound of formula (I) or one of its pharmaceutically-acceptable salts.

The features and advantages of the invention will emerge more clearly in the light of the following examples of implementation, provided for illustrative purposes only and in no way limitative of the invention, with the support of FIGS. 1 to 8, in which:

FIG. 7 shows a graph representing the rate of survival of insects of the species *Bombyx mori* infected with bacteria of the species *P. aeruginosa*, as a function of the administrated dose of a compound (Ia) according to the invention;

and FIG. 8 shows graphs representing the bacterial load in the tissues of various organs of a model mouse infected by *B. cereus*, respectively the lung (a/), the liver (b/) and the spleen (c/), after administration of a dose of 12 mg/kg of a compound according to the invention (Ia).

A/Inhibition of Mfd ATPase Activity In Vitro

For this in vitro assay, the following compounds were used:

compound (Ia) according to the invention, having the formula:

(Ia)

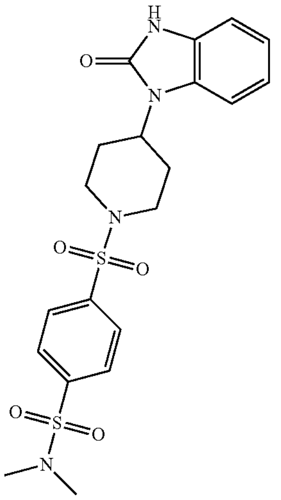

compound (Ib) according to the invention, having the formula:

(Ib)

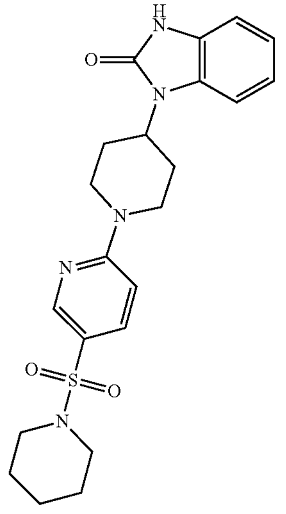

and comparative compounds (IIa) and (IIb), the chemical formulae of which do not fall within general formula (I), but are close to this general formula:

(IIa)

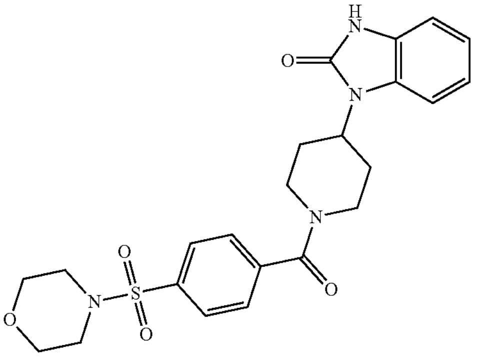

(IIb)

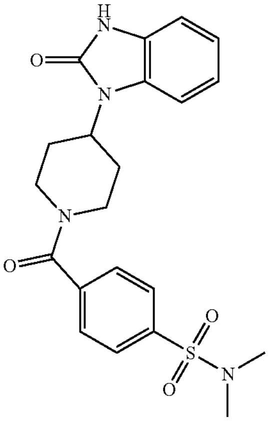

Mfd enzyme activity was evaluated by measuring the quantity of inorganic phosphate ($PO_{4i}$) released using BIOMOL® Green reagent microtiter-plate assay (Enzo Life Sciences). Mfd from *E. coli* (0.35 μM) was incubated with DMSO or with the tested compounds at a concentration of 100 μM in DMSO, for 10 min at 37° C. ATPase reaction was measured in Tris pH8 0.05M; NaCl 0.3M; DTT 0.002M; MgCl2 0.0025M; DMSO 2%; containing ATP (at different concentrations between 0.0022 and 0.279 mM) for 30 min at 37° C. 50 μL of each reaction medium was transferred into clear, flat-bottom 96-well plates and the reaction was terminated by the addition of 100 μl of BIOMOL® Green reagent. The absorbance at 620 nm was measured in a microplate reader (Tecan). The absorbance values were then transformed into nmols of $PO_{4i}$ released based on a $PO_{4i}$ standard curve prepared as recommended by the supplier.

Figure 1:
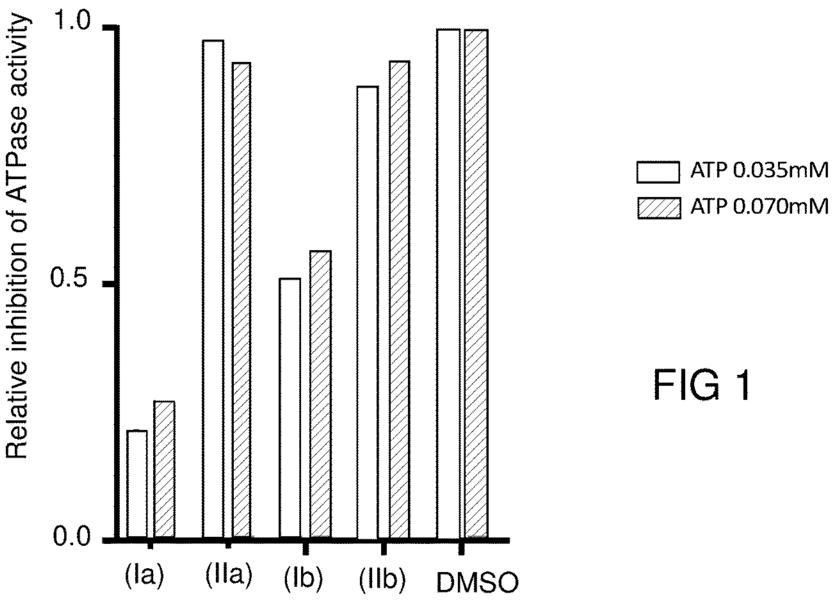
FIG. 1 shows a bar graph representing the relative inhibition of *E. coli* Mfd ATPase activity in vitro, with respect to the vehicle ("DMSO"), by 100 µM of compounds according to the invention (Ia) and (Ib) and by comparative compounds (IIa) and (IIb), respectively for two different ATP concentrations in the medium (0.035 mM and 0.070 mM)

The potency of each compound is calculated relative to the vehicle DMSO control. The results are shown in FIG. 1. Each point is the mean of duplicate experiments of N=2+/−SEM (Standard error of the Mean).

For both ATP concentrations, it can be observed that the compounds of the invention (Ia) and (Ib) exhibit a much higher capacity of inhibition of the Mfd ATPase activity than the comparative compounds, which do not inhibit Mfd ATPase activity. Compound (Ia) is more efficient than compound (Ib).

Mfd ATPase activity at ATP concentrations ranging from 0 to 0.279 mM was measured in the same conditions as described above, without and with presence of various doses of compound (Ia): 0 μM, 3 μM, 10 μM, 30 μM, 65 μM and 100 μM. Curves were fit to the Michaelis-Menten equation with the GraphPad PRISM software. Results are the mean of duplicate experiment of N=3-10+/−SEM.

Figure 2:
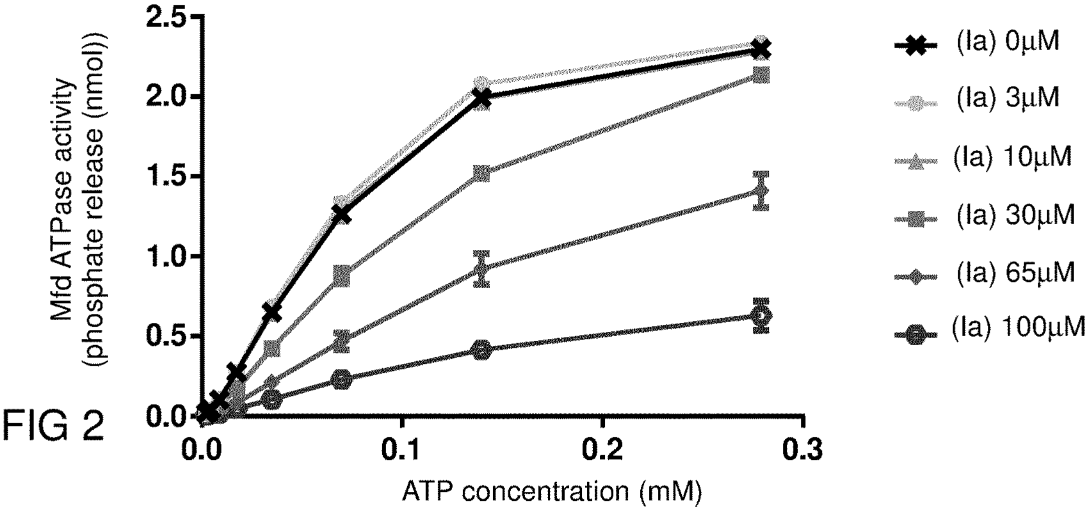
FIG. 2 is a graph showing in vitro *E. coli* Mfd ATPase activity, expressed in terms of phosphate release (nmol) as a function of ATP concentration, in the presence of different doses of a compound according to the invention (Ia)

The results obtained are shown on FIG. 2. They show that compound (Ia) of the invention works as a competitive inhibitor of Mfd ATPase activity.

The Ki of compound (Ia) was calculated at a value of 27.32 μM.

These results demonstrate the high capability of compound (Ia) of the invention to inhibit Mfd ATPase activity.

B/Antimicrobial Activity During Nitric Oxide Stress

The following assay was carried out in order to evaluate whether the compound of the invention (Ia) can inhibit Mfd function in the bacterial resistance against nitric oxide stress.

The power of compound (Ia) to inhibit bacterial growth, specifically in the presence of in vitro-produced nitric oxide, is measured for different bacterial species: *Bacillus cereus* and two antibiotherapy challenging bacteria, regarding medical interest and therapeutic needs, namely *Klebsiella pneumoniae* and *Acinetobacter baumannii.*

Gram-positive *B. cereus* (Bc 407) and Gram-negative *K. pneumoniae* (CIP700603) and *A. baumannii* (CIP7034) strains were grown to exponential phase in Luria-Bertani (LB) medium. Bacteria solution were prepared in Roswell Park Memorial Institute (RPMI) medium and 150 μL were dispatched into 96-wells plate. To measure effect of compound (Ia), bacteria were exposed to 50 μL of NO at a concentration that induces a survival below 90% compared to the condition without NO, in absence (0 μM) or presence (at a dose ranging from 10 to 200 μM) of compound (Ia).

Bacteria survival rate was quantified after 4 h at 37° C. by normalizing bacterial load in (Ia)-treated samples against that in DMSO-treated samples (0 μM of (Ia)).

Figure 3:
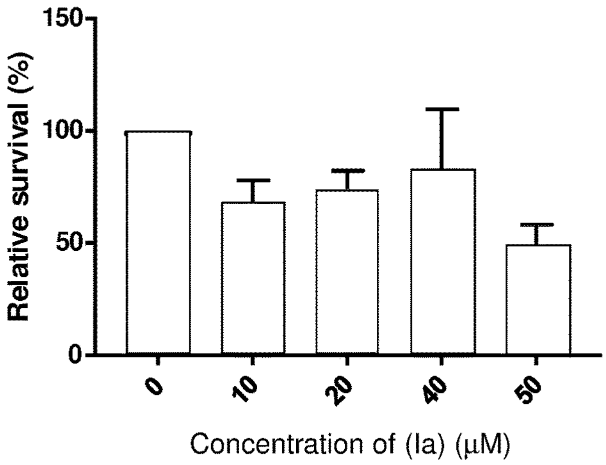
FIG. 3 shows a bar graph representing the relative survival rate of *B. cereus* after 4 h of culture under nitric oxide stress in the presence of different concentrations of a compound according to the invention (Ia), with respect to the vehicle alone (0 µM of (Ia))
Figure 4:
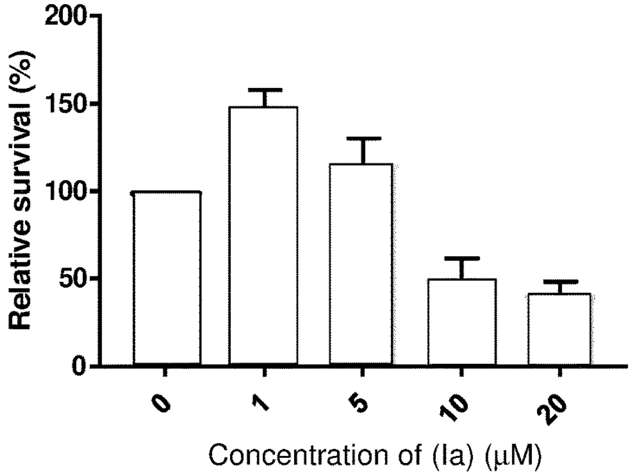
FIG. 4 shows a bar graph representing the relative survival rate of *K. pneumoniae* after 4 h of culture under nitric oxide stress in the presence of different concentrations of a compound according to the invention (Ia), with respect to the vehicle alone (0 µM of (Ia))
Figure 5:
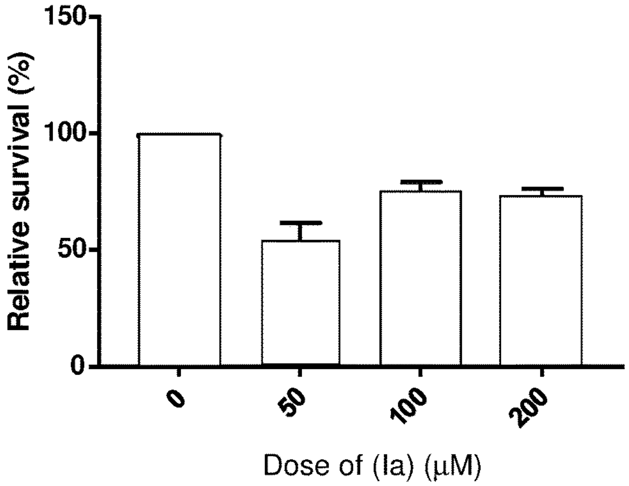
FIG. 5 shows a bar graph representing the relative survival rate of *A. baumanii* after 4 h of culture under nitric oxide stress in the presence of different concentrations of a compound according to the invention (Ia), with respect to the vehicle alone (0 µM of (1a))

The results obtained are shown in FIG. 3 for *B. cereus*, in FIG. 4 for *K. pneumoniae* and in FIG. 5 for *A. baumanii*. In these bar graphs the data represent the mean of duplicate experiment of N=3/12+/−SEM. Two-tailed t-student tests are employed to investigate statistical differences, using GraphPad Prism.

These results show that compound (Ia) of the invention reduces bacteria resistance to NO in vitro for Gram-positive (*B. cereus*) as well as for Gram-negative (*K. pneumoniae* and *A. baumanii*) bacteria. Compound (Ia) reduces bacterial survival during nitric oxide stress.

C/Therapeutic Efficiency In Vivo for Treating Bacterial Infection in Insects

The following experiment was carried out in order to evaluate whether compound (Ia) of the invention can decrease the bacteria virulence in vivo, in silkworm larvae.

Silkworm larvae were infected with Gram-positive *Bacillus cereus* (Bc 407) or Gram-negative *Pseudomonas aeruginosa* (CIP27853) bacteria, as follows.

*Bombyx mori* larvae at the 3rd-4th instar stage (having a weight between 0.7 and 1 g) were used. Larvae were starved for 5 h before the experiment.

*B. cereus* bacteria ($1\times10^2$CFU) or *P. aeruginosa* bacteria ($1\times10^4$CFU) were injected into the larvae (n=10) in absence (0 μM) or in presence of compound (Ia) of the invention, which was injected concomitantly with the bacteria, at different doses ranging between 0.3 and 5.5 μg/g of larvae. The numbers of surviving larvae after 24 h at 27° C. were measured.

Figure 6:
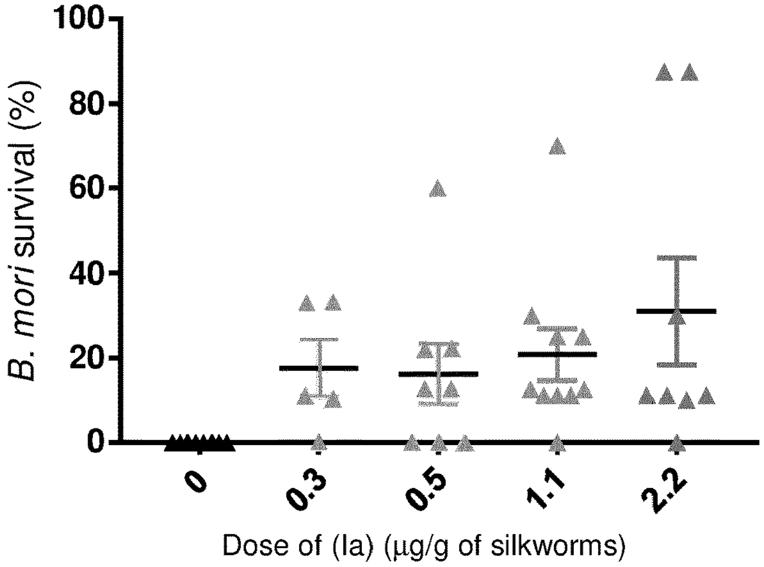
FIG. 6 shows a graph representing the rate of survival of insects of the species *Bombyx mori* infected with bacteria of the species *B. cereus*, as a function of the administrated dose of a compound (Ia) according to the invention.

The results are shown in FIG. 6 for *B. cereus* and in FIG. 7 for *P. aeruginosa*. In these graphs, the data represent the mean of duplicate experiment of N=2/10+/−SEM. Two-tailed t-student tests are employed to investigate statistical differences, using GraphPad Prism.

Compound (Ia) of the invention shows no toxicity towards the insects and, as can be seen on the figures, it provides a significant protective effect against infection with

*B. cereus*, as well as against infection with *P. aeruginosa* at higher doses. These results demonstrate the in vivo innocuity of the compound of the invention and its efficacy for preventing bacteria from killing silkworms.

D/Efficiency In Vivo for the Treatment of an Infection by *B. cereus* in a Mouse Model The efficiency of the compound of the invention (Ia) against a bacterial pathogen was assessed in a mouse model of infection (systemic infection model).

Eight weeks old female C57BL/6JRj (Janvier Labs) mice were infected with *B. cereus* (Bc 407) ($4\times10^6$ CFU) by intraperitoneal injection (100 μL). 100 μl of compound of the invention (Ia) in DMSO at a dose of 12 mg/kg, or of the vehicle alone (DMSO), were further injected to the mice by intraperitoneal injection.

6 h after the infection mice were sacrificed by cervical dislocation. Mice organs were collected and homogenized in cold Phosphate Buffered Saline (PBS). Bacteria burdens in organs were determined by plating serially dilution of the homogenate on LB agar media.

The results obtained are shown on FIG. 8 in a/ for the lung, in b/ for the liver and in c/ for the spleen. In these figures, the data are represented as mean+/−SEM from 3 different experiments with 6-8 mice per group. Each point represents one animal.

It is observed that compound (Ia) of the invention decreases the bacterial load in all these organs following infection by *B. cereus.*

The invention claimed is:

1. A method of treating a bacterial infection in a subject, comprising administering to the subject a therapeutically-effective amount of a compound having the general formula (I):

(I)

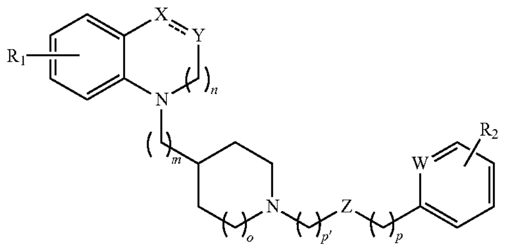

wherein
- m is an integer between 0 and 2,
- n is equal to 0 or 1,
- is equal to 0 or 1,
- p is an integer between 0 and 2,
- p' is an integer between 0 and 2, either the double line ═══ represents a single bond and X is selected from the group consisting of an oxygen atom, $CH_2$, NH, N—$R_5$ and —NCO—$R_5$, wherein $R_5$ represents a linear, branched and/or cyclic, saturated or unsaturated, hydrocarbon-based radical, optionally substituted, optionally comprising one or several heteroatoms and/or one or more groups containing one or more heteroatoms, and Y represents a methylene group, a carbonyl group, a thiocarbonyl group or a C═N—$R_9$ group wherein $R_9$ represents a hydrogen atom or an alkyl or aryl group, or the double line ═══ represents a double bond and X represents a nitrogen atom and Y represents a methine group, Z represents a covalent bond, a methylene group, a sulfonyl group, an amide group, an ester group, an ether group or a carbonyl group, provided that Z does not represent a carbonyl group when p is equal to 0, W represents a nitrogen atom or a C—$R_{10}$ group wherein $R_{10}$ represents a hydrogen atom or a linear, branched and/or cyclic, saturated or unsaturated, hydrocarbon-based radical, optionally substituted, optionally comprising one or several heteroatoms and/or one or more groups containing one or more heteroatoms, $R_1$ is selected from the group consisting of a hydrogen atom, a halogen atom, a hydroxyl group, a primary amine group, a linear or branched and/or cyclic saturated or unsaturated carbon-based radical, optionally aromatic, optionally substituted, optionally comprising one or several heteroatoms and/or one or more groups containing one or more heteroatoms, a —O—$R_6$, —NH—$R_6$ or —NH—CO—$R_6$ group wherein $R_6$ represents a linear, branched and/or cyclic, saturated or unsaturated, hydrocarbon-based radical, optionally substituted, optionally comprising one or several heteroatoms and/or one or more groups containing one or more heteroatoms, and an —NR—$R_5$ group wherein $R_7$ and $R_8$, which may be identical or different, each represent a linear, branched and/or cyclic, saturated or unsaturated, hydrocarbon-based radical, optionally substituted, optionally comprising one or several heteroatoms and/or one or more groups containing one or more heteroatoms, and $R_2$ is selected from the group consisting of a hydrogen atom, a halogen atom, a hydroxyl group, a sulfonic acid group, a primary amine group, and a linear, branched and/or cyclic, saturated or unsaturated, carbon-based radical, optionally substituted, optionally aromatic, optionally comprising one or several heteroatoms and/or one or more groups containing one or more heteroatoms, or one of the pharmaceutically acceptable salts thereof.

2. The method of claim 1, wherein X is selected from the group consisting of $CH_2$, NH, N-alkyl and NCO-alkyl.

3. The method of claim 1, wherein $R_1$ is selected from the group consisting of a hydrogen atom, a halogen atom, a hydroxyl group, a carbonitrile group, a trifluoromethyl group, a carboxyl group, a primary amine group and an alkyl, alkoxy, aryl, arylalkyl, acyl, —CO—O-alkyl, —NH-alkyl or —NH—CO-alkyl group, all of which may optionally be substituted.

4. A method of treating a bacterial infection in a subject, comprising administering to the subject a therapeutically-effective amount of a compound having the general formula (I):

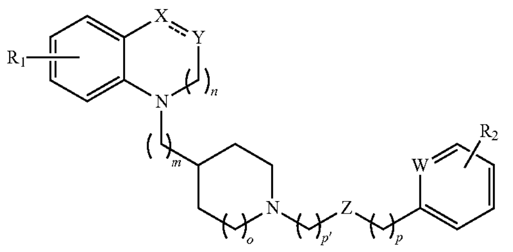

(I)

wherein m is an integer between 0 and 2, n is equal to 0 or 1 is equal to 0 or 1, p is an integer between 0 and 2, p' is an integer between 0 and 2, either the double line ⩦ represents a single bond and X is selected from the group consisting of an oxygen atom, $CH_2$, NH, N—$R_5$ and —NCO—$R_5$ wherein $R_5$ represents a linear, branched and/or cyclic, saturated or unsaturated, hydrocarbon-based radical, optionally substituted, optionally comprising one or several heteroatoms and/or one or more groups containing one or more heteroatoms, and Y represents a methylene group, a carbonyl group, a thiocarbonyl group or a C═N—$R_2$ group wherein $R_5$ represents a hydrogen atom or an alkyl or aryl group, or the double line ⩦ represents a double bond and X represents a nitrogen atom and Y represents a methine group, Z represents a covalent bond, a methylene group, a sulfonyl group, an amide group, an ester group, an ether group or a carbonyl group, provided that Z does not represent a carbonyl group when p is equal to 0, W represents a nitrogen atom or a C—$R_{10}$ group wherein $R_{10}$ represents a hydrogen atom or a linear, branched and/or cyclic, saturated or unsaturated, hydrocarbon-based radical, optionally substituted, optionally comprising one or several heteroatoms and/or one or more groups containing one or more heteroatoms, $R_1$ is selected from the group consisting of a hydrogen atom, a halogen atom, a hydroxyl group, a primary amine group, a linear or branched and/or cyclic saturated or unsaturated carbon-based radical, optionally aromatic, optionally substituted, optionally comprising one or several heteroatoms and/or one or more groups containing one or more heteroatoms, a —O—$R_6$, —NH—$R_6$ or —NH—CO—$R_6$ group wherein $R_6$ represents a linear, branched and/or cyclic, saturated or unsaturated, hydrocarbon-based radical, optionally substituted, optionally comprising one or several heteroatoms and/or one or more groups containing one or more heteroatoms, and an —NR—$R_5$ group wherein $R_7$ and $R_8$, which may be identical or different, each represent a linear, branched and/or cyclic, saturated or unsaturated, hydrocarbon-based radical, optionally substituted, optionally comprising one or several heteroatoms and/or one or more groups containing one or more heteroatoms, and $R_2$ represents a —$SO_2$—$NR_3R_4$ radical, wherein $R_3$ and $R_4$ are identical or different linear or branched alkyl groups or $R_3$ and $R_4$ are linked to form a ring together with the nitrogen atom to which they are attached, or one of the pharmaceutically acceptable salts thereof.

5. A method of treating a bacterial infection in a subject, comprising administering to the subject a therapeutically-effective amount of a compound having the formula (Ia):

(Ia)

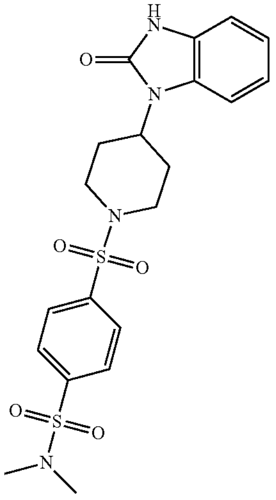

or one of the pharmaceutically acceptable salts thereof.

6. The method of claim 1, which is for inhibiting the Mfd activity of a pathogenic bacteria infecting said subject.

7. The method of claim 1, wherein said bacterial infection is caused by Gram-negative and/or Gram-positive bacteria.

8. The method of claim 1, wherein said compound is administered by oral, parenteral, topical, intranasal, rectal or pulmonary route to said subject.

9. The method of claim 1, wherein said compound is administered once daily to said subject.

10. The method of claim 1, wherein said compound is administered twice daily to said subject.

11. The method of claim 1, wherein said compound is comprised in a pharmaceutical composition, in a pharmaceutically acceptable vehicle.

12. The method of claim 11, wherein said pharmaceutical composition is suitable for administration by oral, parenteral, topical, intranasal, rectal or pulmonary route.

13. The method of claim 1, wherein said compound is encapsulated in nanoparticles.

14. The method of claim 4, wherein $R_3$ and $R_4$ are methyl groups.

* * * * *